(12) United States Patent
Fossa

(10) Patent No.: US 6,716,875 B1
(45) Date of Patent: *Apr. 6, 2004

(54) SYNERGISTIC THERAPEUTIC COMPOSITIONS OF ACE AND RENIN INHIBITORS AND METHODS

(75) Inventor: Anthony Andrea Fossa, North Stonington, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/465,660

(22) Filed: Jun. 5, 1995

Related U.S. Application Data

(60) Division of application No. 07/938,126, filed as application No. PCT/US91/02733 on Apr. 22, 1991, now abandoned, which is a continuation-in-part of application No. 07/522,360, filed on May 11, 1990, now abandoned.

(51) Int. Cl.$^7$ .................. A61K 31/27; A61K 31/40; A61K 31/415; A61K 31/41
(52) U.S. Cl. .................. 514/481; 514/485; 514/423; 514/381; 514/382; 514/408; 514/412; 514/404; 514/424
(58) Field of Search .................. 514/381, 423, 514/385, 408, 409, 412, 404, 419, 424

(56) References Cited

U.S. PATENT DOCUMENTS

| | | | |
|---|---|---|---|
| 4,046,889 A | 9/1977 | Ondetti et al. | 424/244 |
| 4,355,040 A | 10/1982 | Furukawa et al. | 424/273 |
| 4,374,829 A | 2/1983 | Harris et al. | 424/177 |
| 4,749,688 A | 6/1988 | Haslanger et al. | 514/19 |
| 4,814,342 A | 3/1989 | Hoover et al. | 514/385 |
| 4,880,804 A | 11/1989 | Carini et al. | 514/234.5 |
| 4,895,834 A | 1/1990 | Hudspeth et al. | 514/18 |
| 4,962,105 A | 10/1990 | Ksander et al. | 514/212 |

FOREIGN PATENT DOCUMENTS

| | | |
|---|---|---|
| EP | 253310 | 1/1988 |
| EP | 323841 | 7/1989 |
| EP | 324377 | 7/1989 |
| EP | 364804 | 4/1990 |

OTHER PUBLICATIONS

Blaine, E. H. et al., *Hypertension 7*, Suppl. I:I–66 to I–71 (1985).
Mento, P. F. et al., *Hypertension 13*:741–748 (1989) (C.A. III (9) Aug. 28, 1989, Abst. No. 70591c).
Oldham, A. A. et al., *J. Cardiovasc. Pharmacol.* 6:672–677 (1984).
Pals, D. T. et al., *Clin. and Exper. Hyper.—Theory and Practice A13*:425–436 (1991).
Smith III, S. G. et al., *Hypertension* 9:150–156 (1987).
Sweet, C. S. et al., *J. Cardiovasc. Pharmacol.* 6:1067–1075 (1984).
Timmermans, P. B. M. W. M. et al., *Blood Vessels* 27:295–300 (1990).
Tree, M. et al., *J. Hypertension* 7:S51–S55 (1989).
Wong, P. C. et al., *J. Pharmacology and Experimental Therapeutics* 252:719–725 (1990).
Wood, J. M. et al., *J. Cardiovasc. Pharmacol.* 16(Suppl 4):S60–S64 (1990).
Wood, J. M. et al., *J. Hypertension* 7:S37–S42 (1989).
Wood, J. M. et al., *Journal of Pharmacology and Experimental Therapeutics* 253:513–517 (1990).

*Primary Examiner*—Theodore J. Criares
(74) *Attorney, Agent, or Firm*—P. C. Richardson; P. H. Ginsburg; R. L. Catania

(57) ABSTRACT

This invention relates to compositions and methods for achieving a therapeutic effect such as lowering blood pressure and treating congestive heart failure in a mammal. More specifically, this invention relates to synergistic compositions comprising amounts of at least two therapeutic agents selected from the group consisting of a renin inhibitor, an angiotensin I converting enzyme inhibitor and an angiotensin II antagonist, which inhibitors and antagonists are present in amounts sufficient to cause synergistic therapeutic effects such as lowering blood pressure and treating congestive heart failure in a mammal. Further, this invention relates to methods for achieving synergistic therapeutic effects such as lowering blood pressure and treating congestive heart failure in a mammal which methods comprise administering to said mammal, either sequentially in any order or simultaneously, amounts of at least two therapeutic agents selected from the group consisting of a renin inhibitor, an angiotensin I converting enzyme inhibitor and an angiotensin II antagonist, in amounts sufficient to achieve a synergistic therapeutic effect.

7 Claims, No Drawings

SYNERGISTIC THERAPEUTIC COMPOSITIONS OF ACE AND RENIN INHIBITORS AND METHODS

CROSS REFERENCE TO RELATED APPLICATIONS

This application is a division of application Ser. No. 07/938,126, filed Oct. 26, 1992 now abandoned which is the national stage of International Application No. PCT/US91/02733 having an international filing date of Apr. 22, 1991, which is a continuation-in-part of application Ser. No. 07/522,360, filed May 11, 1990, now abandoned.

BACKGROUND OF THE INVENTION

This invention relates to compositions and methods for achieving a therapeutic effect such as lowering blood pressure and treating congestive heart failure in a mammal. More specifically, this invention relates to synergistic compositions comprising amounts of at least two therapeutic agents selected from the group consisting of a renin inhibitor, an angiotensin I converting enzyme inhibitor and an angiotensin II antagonist, which inhibitors and antagonists are present in amounts sufficient to cause synergistic therapeutic effects such as lowering blood pressure and treating congestive heart failure in a mammal. Further, this invention relates to methods for achieving synergistic therapeutic effects such as lowering blood pressure and treating congestive heart failure in a mammal which methods comprise administering to said mammal, either sequentially in any order or simultaneously, mounts of at least two therapeutic agents selected from the group consisting of a renin inhibitor, an angiotensin I converting enzyme inhibitor and an a antagonist II antagonist, in amounts sufficient to achieve a synergistic therapeutic effect.

Examples of renin inhibitors which inhibit the angiotensinogen cleaving action of the enzyme renin are described in U.S. Pat. No. 4,814,342 and U.S. Pat. No. 4,895,834. The teachings thereof are incorporated herein by reference. Such renin inhibitors, among others, are useful in lowering blood pressure in a mammal and in treating congestive heart failure as well as for achieving other therapeutic effects.

Examples of inhibitors of angiotensin I converting enzymes are described in U.S. Pat. No. 4,046,889 and 4,374,829. The. teachings thereof are incorporated herein by reference Among the known angiotensin I converting enzyme inhibitors are captopril, enalapril, lisinopril and ramipril. Such angiotensin I converting enzyme (ACE) inhibitors, among others, are useful in lowering blood pressure in a mammal and in treating congestive heart failure as well as for achieving other therapeutic effects.

Examples of angiotensin II antagonists (AII antagonists) are described in U.S. Pat. No. 4,355,040, U.S. Pat. No. 4,880,804EP 253310, EP 323841 and EP 324377. The teachings thereof are incorporated herein by reference. Included among the known AII antagonists is Dup753. Such AII antagonists, among others, are useful in lowering blood pressure in a mammal and in treating congestive heart failure.

A study has been reported comparing the effects of a renin inhibitor known as H77 with the effects of an ACE inhibitor, captopril. Tree, M., et al., J. Hyper-tension 7: 351–355 (1989). That study suggests, inter alia, that, due to the similar effects achieved, the renin inhibitor and ACE inhibitor act by the same mechanism of reducing angiotensin II. Another study has been reported comparing the hemodynamic effects of MK-422, an ACE inhibitor, and a renin inhibitor and concludes that the responses under study to each were identical. Sweet, C. S., et al., J. Cardiovasc. Pharmacol. 6: 1067–1075 (1984). Yet another study comparing the effect of the renin inhibitor H77 with the ACE inhibitor captopril is reported in Oldham, A. A., et al., J. Cardiovasc. Pharmacol. 6: 672–677 (1984). In that study it is reported that injection of captopril during H77 infusion had a small additional hypotensive effect.

Until the invention described herein, there was no report of use of a renin inhibitor together with an ACE inhibitor to achieve a synergistic blood pressure lowering effect or any other synergistic therapeutic effects such as a congestive heart failure treating effect by employing amounts of a renin inhibitor and an ACE inhibitor.

Further, until this invention, there was no report of use or intent to use a renin inhibitor together with an AII antagonist, an ACE inhibitor together with an AII antagonist or a renin inhibitor together with an ACE inhibitor and an AII antagonist to achieve synergistic therapeutic effects such as a synergistic blood pressure lowering effect or a synergistic congestive heart failure treating effect.

SUMMARY OF THE INVENTION

This invention relates to methods and compositions useful for achieving synergistic therapeutic effects such as lowering the blood pressure of a mammal in need thereof and treating congestive heart failure in a mammal. More specifically, this invention relates to methods for lowering blood pressure in a mammal in need thereof which comprise administering amounts of at least two therapeutic agents selected from the group consisting of a renin inhibitor, an angiotensin I converting enzyme inhibitor and an angiotensin II antagonist to the mammal. This invention also relates to compositions useful for administering amounts of at least two therapeutic agents selected from the group consisting of a renin inhibitor, an angiotensin I converting enzyme inhibitor and an angiotensin II antagonist to a mammal in need thereof. This invention further relates to methods for treating congestive heart failure in a mammal which comprise administering to said mammal amounts of at least two therapeutic agents selected from the group consisting of a renin inhibitor, an angiotensin I converting enzyme inhibitor and an angiotensin II antagonist.

DETAILED DESCRIPTION OF THE INVENTION

The term "synergistic" as used herein means that the effect achieved with the methods and compositions of this invention is greater than the sum of the effects that result from methods and compositions comprising the inhibitors and antagonists of this invention separately and in the amounts employed in the methods and compositions hereof.

According to one aspect:of this invention, it is now possible to achieve a synergistic therapeutic effect in a mammal with amounts of a renin inhibitor and an ACE inhibitor which, if administered in said amounts singly, are not capable of achieving said effect and which effect is greater than the sum of the effects achieved for each inhibitor separately. Preferred therapeutic effects achieved according to this aspect of the invention are lowering of blood pressure in a mammal in need thereof and treating congestive heart failure in a mammal. The administration of the renin inhibitor and the ACE inhibitor can be sequential in time or simultaneous with the simultaneous method being preferred. For sequential administration, the renin inhibitor can be administered before or after administration of the ACE inhibitor but it is preferable to administer the renin inhibitor before the ACE inhibitor.

According to another aspect of this invention, it is now possible to achieve a synergistic therapeutic effect in a mammal with amounts of a renin inhibitor and an AII antagonist which, if administered in said amounts singly, are not capable of achieving said effect and which effect is greater than the sum of the effects achieved for the inhibitor and the antagonist separately. Preferred therapeutic effects achieved according to this aspect of the invention are lowering of blood pressure in a mammal in need thereof and treating congestive heart failure in a mammal. The administration of the renin inhibitor and the AII antagonist can be sequential in time or simultaneous with the simultaneous method being preferred. For sequential administration, the renin inhibitor can be administered before or after administration of the AII antagonist but it is preferable to administer the renin inhibitor before the AII antagonist.

According to yet another aspect of this invention, it is now possible to achieve a synergistic therapeutic effect in a mammal with amounts of an ACE inhibitor and an AII antagonist which, if administered in said amounts singly, are not capable of achieving said effect and which effect is greater than the sum of the effects achieved for the inhibitor and the antagonist separately. Preferred therapeutic effects achieved according to this aspect of the invention are lowering of blood pressure in a mammal in need thereof and treating congestive heart failure in a mammal. The administration of the ACE inhibitor and the AII antagonist can be sequential in time or simultaneous with the simultaneous method being preferred. For sequential administration, the ACE inhibitor can be administered before or after administration of the AII antagonist but it is preferable to administer the ACE inhibitor before the AII antagonist.

According to still yet another aspect of this invention, it is now possible to achieve a synergistic therapeutic effect in a mammal with amounts of a renin inhibitor, an ACE inhibitor and an AII antagonist which, if administered in said amounts singly, are not capable of achieving said effect and which effect is greater than the sum of the effects achieved for the inhibitors and the antagonist separately. Preferred therapeutic effects achieved according to this aspect of the invention are lowering of blood pressure in a mammal in need thereof and treating congestive heart failure in a mammal. The administration of the renin inhibitor, ACE inhibitor and AII antagonist can be sequential in time, simultaneous with respect to any two thereof or simultaneous with respect to all three. It is preferred that such administration be simultaneous with respect to all three. For sequential administration the inhibitors and the antagonist can be administered in any order. However, it is preferable for such sequential administration that the renin inhibitor be administered before the ACE inhibitor to which, in turn, is administered before the AII antagonist.

Because of the synergistic therapeutic effects achieved by administration of a renin inhibitor and/or an ACE inhibitor and/or an AII antagonist, this invention provides particularly advantageous methods of achieving a therapeutic blood pressure lowering effect or treatment of congestive heart failure with less than therapeutic levels of a renin inhibitor and/or an ACE inhibitor and/or an AII antagonist. Thetefore, in practicing this invention, it i possible to minimize potential adverse effects which may be associated with larger, therapeutic doses of the renin inhibitor, the ACE inhibitor and/or the AII antagonist and still achieve a therapeutic blood pressure lowering or congestive heart failure treating effect.

The compositions of this invention comprise an amount of a renin inhibitor; or an amount of an ACE inhibitor; or an amount of an AII antagonist; or an amount of a renin inhibitor and an amount ACE inhibitor; or an amount of a renin inhibitor and an amount AII antagonist; or an amount of an ACES inhibitor and an amount AII antagonist; or an amount of a renin inhibitor, an amount of an ACE inhibitor and an amount of an AII antagonist; and a pharmaceutically-acceptable diluents or carrier. The amounts of the renin inhibitor, the ACE inhibitor and the AII antagonist in such compositions are such that each, separately, is not present in an amount sufficient to result in the level of therapeutic effect achieved when combinations of two or more thereof are administered to a mammal.

The compositions comprising an amount of a renin inhibitor according to this invention are useful for administration to a mammal in combination with the administration of a composition according to this invention comprising an ACE inhibitor or an AII antagonist or an ACE inhibitor and an AII antagonist.

The compositions comprising an amount of an AII inhibitor according to this invention are useful for administration to a mammal in combination with the administration of a composition according to this invention comprising a renin inhibitor or an AII antagonist or a renin inhibitor and an AII antagonist.

The compositions comprising an amount of an AII antagonist according to this invention are useful for administration to a mammal in combination with the administration of a composition according to this invention comprising a renin inhibitor or an antagonist or a renin inhibitor and an AII antagonist.

A particular advantage of the present invention is that the compositions hereof can comprise amounts of a renin inhibitor and/or an ACE inhibitor and/or an AII antagonist which are less that those required for compositions containing only a renin inhibitor or an ACE inhibitor or an AII antagonist. Therefore, compositions comprising reduced amounts of a renin inhibitor and/or an ACE inhibitor and/or an AII antagonist according to this invention afford compositions with reduced side effects which may be associated with amounts of the renin inhibitor or the ACE inhibitor or the AII antagonist necessary to achieve the same therapeutic effects as the compositions of this invention.

The present invention is not limited in any way to specific renin inhibitors and/or ACE inhibitors and/or AII antagonists but is applicable to all such renin inhibitors, ACE inhibitors and AII antagonists now known or subsequently discovered or developed. It is the co-administration of a renin inhibitor and an ACE inhibitor, or a renin inhibitor and an AII antagonist, or an ACE inhibitor and an AII antagonist or a renin inhibitor, an ACE inhibitor and an AII antagonist as taught by this invention and not the particular renin inhibitor or ACE inhibitor or AII antagonist which brings about the synergistic effect of this invention. Nonetheless, a preferred renin inhibitor for use in the methods and compositions of this invention is [alpha-R[alpha-R*,beta-S*(S*, S*)]-alpha-hydroxy-beta-[[2-[[2-(4-morpholin-1-carboxamido)-1-oxo-3-phenylpropyl]amino]-3-methylthio-1-oxo-propyl]amino]cyclohexanebutanoic acid, isopropyl ester; preferred ACE inhibitors are captopril, enalapril, lisinopril and ramipril; and a preferred AII antagonist is. Dup753. Particularly preferred ACE inhibitors for use in the methods and compositions of this invention are captopril and enalapril.

As discussed above, it is now possible through the practice of this invention to achieve certain desired therapeutic effects using less of a renin inhibitor and/or an ACE inhibitor and/or an AII antagonist than was heretofore possible. The desired therapeutic effects achievable through the practice of this invention include, but are not limited to, lowering of blood pressure and/or treating of congestive heart failure in a mammal. Prior to this invention it was known that a certain amount of an ACE inhibitor or a certain amount of an AII antagonist or a certain amount of a renin inhibitor was necessary to achieve desired therapeutic effects Now, according to this invention, an amount of a renin inhibitor less than that necessary to achieve said therapeutic effects can be co-administered with an amount of an ACE inhibitor and/or an amount of an AII antagonist, which amount or amounts are less than that necessary to achieve said therapeutic effects, with the result that synergistic therapeutic effects, equal to or greater than said therapeutic effects are achieved. Further, according to this invention, an amount of an ACE inhibitor less than that necessary to achieve said therapeutic effects can be co-administered with an amount of an AII antagonist and/or an amount of a renin inhibitor which amount or amounts are less than that necessary to achieve said therapeutic effects with the result that synergistic therapeutic effects equal to or greater than said therapeutic effects are achieved. Further, and significantly, the synergistic therapeutic effects achieved through the use of the methods and compositions of this invention are greater than the sum of the effects achieved through the use of methods and compositions employing either a renin inhibitor or an ACE inhibitor or an AII antagonist-alone in amounts equal to the amounts used in the methods and compositions herein.

In practicing the methods of this invention, which comprise administering, simultaneously or sequentially and in any order, two or more of, a renin inhibitor and/or an ACE inhibitor and/or an AII antagonist to a mammal, such administration can be orally, bucally, parentally, by inhalation spray, redtally or topically. It is preferred that such, administration be orally It is even more preferred that such administration be orally and simultaneously. The term "parentally" as used herein includes, but is not limited to, subcutaneous, intravenous, intramuscular and intrasternal injections and infusion techniques. When the renin inhibitor and/or the ACE inhibitor and/or the AII antagonist are administered sequentially, the administration of each can be by the same method or by different methods.

The pharmaceutical compositions of this invention include compositions which comprise either a renin inhibitor or an ACE inhibitor or an AII antagonist in an amount less than that necessary to a achieve the desired therapeutic effect together with a pharmaceutically acceptable diluents or carrier and compositions which comprise two or more of a renin inhibitor and an ACE inhibitor and an AII antagonist, each of which is present in an amount which is less than that necessary to achieve the desired therapeutic effect alone, together with a pharmaceutically-acceptable diluents or carrier.

The compounds of this invention can be orally administered in a wide variety of different dosage forms, i.e., they may be formulated with various pharmaceutically acceptable inert carriers in the form of tablets, capsules, lozenges, troches, hard candies, powders, sprays, aqueous suspensions, elixirs, syrups and the like. Such carriers include solid diluents or fillers, sterile aqueous media and various non-toxic organic solvents, etc Moreover, such oral pharmaceutical formulations can be suitably sweetened and/or flavored by means of various agents of the type commonly employed for such purposes. In general, the compounds of this invention are present in such oral dosage forms at concentration levels ranging from about 0.5% to about 90% by weight of the total composition, in amounts which are sufficient to provide the desired unit dosages. Other suitable dosage forms for the compounds of this invention include, but are not limited to, controlled release formulations and devices well known to those who practice in the art.

For purposes of oral administration, tablets containing various excipients such as sodium citrate, calcium carbonate and calcium phosphate may be employed along with various disintegrants such as starch and preferably potato or tapioca starch, alginic acid and certain complex silicate, together with binding agents such as polyvinylpyrrolidone, sucrose, gelatin and acacia. Additionally, lubricating agents such as magnesium stearate, sodium lauryl sulfate and talc or compositions of a similar type may also be employed as fillers in soft and hard-filled gelatin capsules; included lactose or milk sugar as well as high molecular weight polyethylene glycols. When aqueous suspensions and/or elixirs are desired for oral administration, the essential active ingredient therein may be combined with various sweetening or flavoring agents, coloring matter or dyes and, if so desired, emulsifying agents and/or water, ethanol, propylene glycol, glycerin and various like combinations thereof.

Although the preferred mode of administration of the compounds of this invention is oral, they may be administered parentally as well.

For purposes of parenteral administration, solutions of the compounds in sesame or peanut oil or in aqueous propylene glycol maybe employed, as well as sterile aqueous solutions of the corresponding pharmaceutically-acceptable salts. Such aqueous solutions should be suitably buffered if necessary, and the liquid diluents rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluents and the final preparation is passed through a suitable bacterial filter such as a sintered glass filter or a diatomaceous-earth or unglazed porcelain filter. Preferred filters of this type include the Berkefeld, the Chamberland and the Asbestos Disk-Metal Seitz filter, wherein the fluid is sucked into a sterile container with the aid of a suction pump. The necessary steps should be taken throughout the preparation of these injectable solutions to insure that the final products are obtained in a sterile condition For purposes of transdermal administration, the dosage form of the particular compound or compounds may include, by way of example, solutions, lotions, ointments, creams, gels, suppositories, rate-limiting sustained release formulations and devices therefor. Such dosage forms comprise the particular compound or compounds and may include ethanol, water, penetration enhancer and inert carriers such as gel-producing materials, mineral oil, emulsifying agents, benzyl alcohol and the like. Specific transdermal flux enhancing compositions are disclosed in European Patent Application 271,983 and European Patent Application 331,382 which have been filed in the name of the assignee of this invention, the teachings of which are incorporated herein by reference.

The dosage of the renin inhibitor and/or the ACE inhibitor and/or the AII antagonist necessary to achieve the desired therapeutic effect is within the skill of those who practice in the art having the benefit of the disclosure herein. Dosage ranges for certain renin inhibitors have been reported with representative dosages being 0.250 mg/kg to 1.4 mg/kg I.V. and 40mg/day to 1200 mg/day orally. Dosage ranges for certain ACE inhibitors have been reported with representative dosages of 40 mg/day to 450 mg/day orally and 20 mg/day parentally. Dosage ranges for certain AII antagonists have been reported with representative dosages being about 0.5 to 500 mg/kg p.o., preferably 2 to 80 mg/kg p.o., and 3 mg/kg i.v. The dosages to be employed according to this invention may be varied depending upon the requirements, of the patient, the severity of the condition being treated and the compounds being administered. Further, the daily dosages to be administered may be divided and administered in portions during the day. The dosage or dosages which will result in optimal synergistic effects is achieved by coordinating the, pharmacokinetic properties, such as volume of distribution and $T_{max}$, of the therapeutic agents of this invention so that the therapeutic windows of each agent overlap to the maximum extent possible. Such dosages are readily determined by one skilled in the art enabled by the disclosure herein.

The synergistic effect on blood pressure lowering achieved by co-administration of a renin inhibitor and an ACE inhibitor was demonstrated as described below. The renin inhibitor (RI) used was [alpha-R[alpha-R*, beta-S* (S*,S*)]-alpha-hydroxy-beta-[[-2-[[2-(4-morpholin-1-carboxamido)-1-oxo-3-phenylpropyl]amino]-3-methylthio-1-oxo-propyl]amino]-cyclohexanebutanoic acid, isopropyl ester and is described in U.S. Pat. No. 4,814,342. The ACE inhibitor used was captopril.

Male Hartley guinea pigs weighing between 250 and 300 g were obtained from Charles River Laboratories, Lakeview, N. J. The guinea piqs were allowed to acclimate to their environment for at least two weeks. Then, they were placed on a low sodium diet (Purina Modified Guinea Pig Chow, no sodium added) for 14 days and were given injections of furosemide (Lasixe® 2 mg/kg, i.m.) on three non-consecutive days. At least 24 hours prior to experimentation, the animals were anesthetized with xylazine (Rompun®, 10 mg/kg, s.c.) and ketamine (Vetalare®, 80 mg/kg, i.m.) and, using aseptic technique, cannulae (PE-50) were implanted into the aorta via the right carotid artery for direct measurement of mean arterial pressure (MAP). Cannulae (PE-50) were also placed into the left jugular vein for intravenous compound administration. Both catheters were exteriorized at the intrascapular region of the animal's back and flushed with a heparinized dextrose solution. To prevent the formation of clots, each cannula was filled with heparin at a concentration of 1000 units/ml. After surgery, an antibacterial, trimethoprim/sulfamethoxazole (Di-Trime®, 30 mg/kg, s.c.), was given to the animals. The animals were allowed to recover with water and no-sodium chow administered ad libitum. On the day of the experiment, each guinea pig was given an additional injection of furosemide (6 mg/kg, i.m.) to accelerate sodium loss and was placed in a sound-proof, ventilatedbox with one-way, glass for observation. Mean arterial pressure was monitored with a Statham 23DB strain gauge pressure transducer previously calibrated using a mercury manometer. The arterial pressure waveform and derived heart rate were continuously recorded on a Grass Model 7D oscillograph. Arterial pressure waveform samples were obtained approximately every 20 seconds using an IBM PS/2 model 30 computer equipped with a custom algorithm designed to calculate mean arterial pressure from the integrated waveform. Values were obtained for a period of at least one hour prior to and 2 hours (usually 4 hours) after dosing. The test compounds were infused intravenously followed by a 250 µl flush with heparinized dextrose solution.

Dose response curves for the renin inhibitor (RI) (0.3 to 3.0 mg/kg, i.v.) and captopril (0.03 to 1.0 mg/kg, i.v.) were obtained (n=4 to 8) in order to quantitate baseline responses to each drug. In experiments where the renin inhibitor and captopril were co-administered, the renin inhibitor was given first immediately followed by captopril. Doses of renin inhibitor and angiotensin converting enzyme inhibitor, when given together, were chosen on the basis of causing submaximal hypotensive effects. Therefore, the contributory effect of each drug could be quantitated by integration and compared to the expected effect to. determine whether additive or synergistic responses had occurred.

Employing the procedure described above, the changes in mean arterial pressure (AMAP) for the renin inhibitor (RI), the ACE inhibitor (captopril) and the renin inhibitor (RI), plus the ACE inhibitor (captopril) were obtained for various doses and are shown in Table I, below. The AOC-MAP is the area over the dose response curve for each dose calculated using the trapezoidal method.

TABLE I

| Inhibitor | Dose (mg/kg) | AOC-MAP |
| --- | --- | --- |
| RI | 0.3 | −256 |
|  | 1.0 | −496 |
|  | 3.0 | −1829 |
| captopril | 0.03 | −99 |
|  | 0.10 | −289 |
|  | 0.30 | −1263 |
|  | 1.0 | −3272 |
| RI + captopril | 0.5 + 0.05 | −973 |
| RI + captopril | 1.5 + 0.15 | −4238 |

As shown in Table I, above, co-administration of a renin inhibitor and an ACE inhibitor result in a synergistic effect which effect is much greater than the sum of the effect achieved for each inhibitor separately.

The data in Table I were obtained by averaging the the Δ MAP of all animals for each dose prior to calculating the AOC-MAP. When the data contained in Table I was reviewed for the purpose of calculating the AOC-MAP by averaging the area over the dose response curve for each animal per dose, it was discovered that the AOC-MAP for 0.5 mg/kg RI plus 0.05 mg/kg captopril inadvertently reflected the data based on only three of the six subject test animals. Shown below in Table II are the AOC-MAP data for the experiments reported in Table I, which data is now the result of determining the area over the dose response curve for each animal per dose and averaging the AOC-MAP, as well as determining the standard deviation. In addition, the data for 0.5 mg/kg RI plus 0.05 mg/kg captopril now reflects the results from all six test animals receiving such a dose. The areas over the dose response curves were calculated using the trapezoidal method.

TABLE II

| Inhibitor | Dose (mg/kg) | AOC-MAP |
| --- | --- | --- |
| RI | 0.3 | −310 (±47) |
|  | 1.0 | −568 (±158) |
|  | 3.0 | −1990 (±408) |
| captopril | 0.03 | −96 (±16) |
|  | 0.10 | −283 (±24) |
|  | 0.30 | −1036 (±145) |

TABLE II-continued

| Inhibitor | Dose (mg/kg) | AOC-MAP |
|---|---|---|
|  | 1.0 | −3272 (±350) |
| RI + captopril | 0.5 + 0.05 | −1629 (±259) |
| RI + captopril | 1.5 + 0.15 | −3877 (±426) |

Table II, above, also shows that co-administration of a renin inhibitor and an ACE inhibitor result in a synergistic effect which effect is much greater than the sum of the effect achieved for each inhibitor separately.

Also employing the general procedure described above, the changes in mean arterial pressure, expressed as AOC-MAP, for the ACE inhibitor captopril, the AII antagonist Dup 753 and the ACE inhibitor captopril plus the AII antagonist Dup 753 were obtained for various doses and are shown in Table III, below. In the experiment, where captopril and Dup 753 were co-administered, captopril was given first immediately followed by Dup 753. Doses of captopril and Dup 753, when given together, were chosen on the basis of causing submaximal hypotensive effects separately. The AOC-MAP, as in Table II, above, is the average of the area over the dose response curve for each animal per dose. The areas over the dose response curves were calculated using the trapezoidal method.

TABLE III

| Inhibitor/ Antagonist | Dose (mg/kg) | AOC-MAP |
|---|---|---|
| captopril | 0.13 | −96 (±16) |
|  | 0.10 | −269 (±18) |
|  | 0.30 | −826 (±128) |
|  | 1.0 | −3272 (±350) |
| Dup 753 | 0.3 | −125 (±31) |
|  | 1.0 | −549 (±96) |
|  | 3.0 | −1575 (±281) |
| captopril + Dup 753 | 0.05 + 0.5 | −685 (±79) |

Table III, above, shows that co-administration of an ACE inhibitor and an AII antagonist result in a synergistic-effect which effect is greater than the sum of the effect achieved for the ACE inhibitor and the AII antagonist separately.

What is claimed is:

1. A method for achieving a synergistic therapeutic effect comprising lowering blood pressure or treating congestive heart failure in a mammal in need thereof which comprises administering to said mammal synergistic effective amounts of:
   (a) alpha-R[alpha-R*, beta-S*(S*,S*)]-alpha-hydroxy-beta-[[2-[[2-(4-morpholin-1-carboxamido)-1-oxo-3-phenyl-propyl]amino]-3-methylthio-1-oxo-propyl]amino]cyclohexanebutanoic acid;
   (b) captopril; and
   (c) Dup753,
   wherein the amount of (a) alone, the amount of (b) alone and the amount of (c) alone is insufficient to achieve the therapeutic effect; and
   wherein the combined effect of the amounts of (a), (b) and (c) administered is greater than the sum of the therapeutic effects of the amounts of (a), (b) and (c) individually administered.

2. The method according to claim 1 wherein the therapeutic effect comprises lowering of blood pressure.

3. The method according to claim 1 wherein the therapeutic effect comprises treating congestive heart failure.

4. A pharmaceutical composition for achieving a therapeutic effect comprising lowering blood pressure or treating congestive heart failure in a mammal in need thereof which comprises synergistic effective amounts of:
   (a) alpha-R[alpha-R*, beta-S*(S*,S*)]-alpha-hydroxy-beta-[[2-[[2-(4-morpholin-1-carboxamido)-1-oxo-3-phenyl-propyl]amino]-3-methylthio-1-oxo-propyl]amino]cyclohexanebutanoic acid;
   (b) captopril; and
   (c) Dup753,
   wherein the amount of (a) alone, the amount of (b) alone and the amount of (c) alone is insufficient to achieve the therapeutic effect; and
   wherein the combined effect of the amounts of (a), (b) and (c) is greater than the sum of the therapeutic effects achievable with the amounts of (a), (b) and (c) individually, and a pharmaceutically acceptable diluents or carrier.

5. A first pharmaceutical composition for use with a second pharmaceutical composition for achieving a therapeutic effect comprising lowering blood pressure or treating congestive heart failure in a mammal in need thereof, which effect is greater than the sum of the therapeutic effects achieved by said first and second pharmaceutical compositions separately and which second pharmaceutical composition comprises an amount of an angiotensin I converting enzyme inhibitor and an amount of an angiotensin II antagonist, said first pharmaceutical composition comprising a synergistic effective amount of alpha-R[alpha-R*, beta-S*(S*,S*)]-alpha-hydroxy-beta-[[2-[[2-(4-morpholin-1-carboxamido)-1-oxo-3-phenyl-propyl]amino]-3-methylthio-1-oxo-propyl]amino]cyclohexanebutanoic acid and a pharmaceutically acceptable diluents or carrier.

6. A first pharmaceutical composition for use with a second pharmaceutical composition for achieving a therapeutic effect comprising lowering blood pressure or treating congestive heart failure in a mammal in need thereof, which effect is greater than the sum of the therapeutic effects achieved by said first and second pharmaceutical compositions separately and which second pharmaceutical composition comprises an amount of a renin inhibitor and an amount of an angiotensin II antagonist, said first pharmaceutical composition comprising a synergistic effective amount of captopril and a pharmaceutically acceptable diluents or carrier.

7. A first pharmaceutical composition for use with a second pharmaceutical composition for achieving a therapeutic effect comprising lowering blood pressure or treating congestive heart failure in a mammal in need thereof, which effect is greater than the sum of the therapeutic effects achieved by said first and second pharmaceutical compositions separately and which second pharmaceutical composition comprises an amount of a renin inhibitor and an amount of an angiotensin I converting enzyme inhibitor, said first pharmaceutical composition comprising a synergistic effective amount of Dup753 and a pharmaceutically acceptable diluents or carrier.

* * * * *